(12) United States Patent
Sun et al.

(10) Patent No.: US 9,308,582 B2
(45) Date of Patent: Apr. 12, 2016

(54) SOLUTION STABLE AND CHEMICALLY REACTIVE METALLIC NANOPARTICLES

(76) Inventors: Yi Sun, Wellesley, MA (US); Zhuo Sun, Shanghai (CN)

( * ) Notice: Subject to any disclaimer, the term of this patent is extended or adjusted under 35 U.S.C. 154(b) by 633 days.

(21) Appl. No.: 12/647,244

(22) Filed: Dec. 24, 2009

(65) Prior Publication Data
US 2011/0159291 A1  Jun. 30, 2011

(51) Int. Cl.
| | |
|---|---|
| B32B 5/16 | (2006.01) |
| B82Y 5/00 | (2011.01) |
| B22F 1/00 | (2006.01) |
| B01J 2/00 | (2006.01) |
| B82Y 30/00 | (2011.01) |
| B82Y 40/00 | (2011.01) |
| B05D 3/00 | (2006.01) |

(52) U.S. Cl.
CPC .............. *B22F 1/0088* (2013.01); *B01J 2/006* (2013.01); *B22F 1/0018* (2013.01); *B22F 1/0062* (2013.01); *B82Y 5/00* (2013.01); *B82Y 30/00* (2013.01); *B82Y 40/00* (2013.01); *Y10T 428/2998* (2015.01)

(58) Field of Classification Search
None
See application file for complete search history.

(56) References Cited

U.S. PATENT DOCUMENTS 6,677,122 B2  1/2004  Mirkin et al.
7,588,827 B2  9/2009  Nie et al.

OTHER PUBLICATIONS

Asian, K., Lakowicz, J.R., Geddes, C.D. "Nanogold-plasmon-resonance-based glucose sensing." Analytical Biochemistry 330 (2004): 145-155.*
Asian, K., Zhang, J., Lakowicz, J.R., Geddes, C.D. "Saccharide Sensing Using Gold and Silver Nanoparticles—A Review." Journal of Fluorescence 14.4 (2004): 391-400.*
Doty, R.C., Tshikhudo, T.R., Brust, M., Fernig, D.G. "Extremely Stable Water-Soluble Ag Nanoparticles." Chem. Mater. 17 (2005): 4630-4635.*
Weissleder, R., Kelly, K., Sun, E.Y., Shtatland, T., Josephson, L. "Cell-specific targeting of nanoparticles by multivalent attachment of small molecules." Nature Biotechnology 23.11 (2005): 1418-1423.*
Eck, W., Craig, G., Sigdel, A., Rifter, G., Old, L.J., Tang, L., Brennan, M.F., Allen, P.J., Mason, M.D. "PEGylated Gold Nanoparticles Conjugated to Monoclonal F19 Antibodies as Targeted Labeling Agents for Human Pancreatic Carcinoma Tissue." ACS Nano 2.11 (2008), 2263-2272.*
Murcia, M.J., Naumann, C.A. "Biofunctionalization of Fluorescent Nanoparticles" Nanotechnologies for the Life Sciences. (2007).*

* cited by examiner

*Primary Examiner* — Alicia Chevalier
*Assistant Examiner* — Thomas Mangohig
(74) *Attorney, Agent, or Firm* — Jie Tan; JT Law Services, PC

(57) ABSTRACT

Entity and methods for generating stable and chemically reactive metallic nanoparticles and stable metallic nano-probes. Polymeric coating molecules having at least one metal core binding motif and at least one chemically reactive functional moiety is stably bound to the surface of metallic nanoparticle via the metal core binding motif. A target specific probe molecule is covalently bound to the metallic nanoparticle via the chemically reactive functional moiety forming stable metallic nano-probe.

22 Claims, 5 Drawing Sheets

A: Streptavidin coated gold nanoparticles in 10% NaCl remains stable;

B: Non-coated gold nanoparticles precipate in 10% NaCl solution.

SOLUTION STABLE AND CHEMICALLY REACTIVE METALLIC NANOPARTICLES

BACKGROUND

The present application relates to nanoparticles, and more particularly to metallic nanoparticle suspensions that are stable in buffered aqueous solution and are also chemically reactive under normal temperatures and conditions.

Note that the points discussed below may reflect the hindsight gained from the disclosed inventions, and are not necessarily admitted to be prior art.

Metallic nanoparticles display fascinating properties that are quite different from those of individual atoms, surfaces or bulk materials. Applications, or potential applications, are diverse and interdisciplinary. They include, for example, use in biochemistry, in catalysis and as chemical and biological sensors, in medicine. The properties of the metallic nanoparticles can vary depending on whether they are free, deposited on a surface or embedded in a matrix of another material.

Due to their characteristic easy-to-measure physical properties and chemically inertness, metallic nanoparticles have been used in the fabrication of targeted probes for bioagent detections and separations. Targeted bioagents can include bio-organisms such as virus and bacteria, or bio-molecules such as antigens, antibodies, proteins, nucleic acid, peptides, hormones as well as bioactive small molecules. Probe-attached nanoparticles are used also in vivo to recognize and locate specific ligands in specific tissues or organs.

In order to detect bioagents, target specific ligands, such as antibodies or nucleic acid, need to be attached to the surface of nanoparticles.

Traditionally, targeted specific ligands, such as antibodies, nucleic acid, proteins or peptides were absorbed to the surface of nanoparticles via static, non-specific interactions. The optimal binding conditions depend on many factors including salt concentration, buffer type, pH and stabilizing agents. These methods are tedious, laborsome and time consuming. Nanoparticle probes generated from these methods usually suffer poor stability and the attached probes can easily become detached from the metal nanoparticles.

SUMMARY

The present application discloses new approaches to fabricating target specific ligand conjugated metal nanoparticle system.

A solution stable and chemically reactive metallic nanostructure system is created that can be readily used for stably attaching a variety of target specific probes.

The nanostructure system comprises a solution stable metal nanoparticle suspension, wherein each nanoparticle comprises a metal nanoparticle core and a coating polymer layer on the surface. In one embodiment, the nanoparticle core is a metal particle with a diameter between about 1 nm to 250 nm, preferably between about 5 nm to 100 nm. The metal nanoparticle core may be made of gold, silver, platinum, iron or copper.

In one embodiment, the nanoparticles with metallic core are coated with polymers having at least two chemically active functional groups. At least one side chain of the coating polymer has a metal nanoparticle binding motif and at least one other side chain of the coating polymer has a chemically reactive motif. In one embodiment, the nanoparticle binding motifs comprise reduced or non-reduced sulfhydryl groups. In another embodiment, the chemically reactive motifs comprise one of the aldehyde groups, amino groups, carboxylic groups, epoxy groups, tosyl groups, hydroazide groups or azide groups.

The polymer coating may be selected from natural or synthetic polymers or derivatives of each. Examples include derivatives of sulfhydryl and amino derived dextran, cyclodextran or other polysaccharides, sulfhydryl and amino derived polyethylene glycol, polyvinyl alcohol. Polymer coating can be further cross-linked to provide better stability for the nanostructure system.

The chemically reactive metal nanoparticle system can be synthesized via the steps of (i) obtaining a polymer having bi or multiple functional groups attached to its side chains. These functional groups contain at least one type that can bind to nanoparticle (binding motif) and at least another type that are not bound to nanoparticles and can be used to perform chemical reaction; (ii) attaching the polymer to the nanoparticle metal core via binding motif; (iii) cross-linking the coating polymer molecules with bifunctional cross-linkers; (iv) deriving target specific coated metal nanoparticles with chemically reactive groups.

An example process for conjugating biomolecules to the chemically reactive metal nanoparticles is via the steps of (a) providing a solution of chemically reactive metal nanoparticles in appropriate aqueous buffer; (b) mixing the biomolecule and conjugation reagents with the nanoparticle solution; (c) carrying out the conjugation reaction under proper reaction conditions; (d) removing non-reacted biomolecule ligands.

The disclosed innovations, in various embodiments, provide one or more of at least the following advantages. However, not all of these advantages result from every one of the innovations disclosed, and this list of advantages does not limit the various claimed inventions.

Stabilized suspension of metal nanoparticle solutions for generating conjugated probe system;

Stabilized conjugating of biomolecules to metal nanoparticles;

Increased specificity in biomolecule detection using the derived metal nanoparticle conjugated probes because of the increased stability of the probe system.

Improved ability for in vivo application of the derived metal nanoparticle detection system.

BRIEF DESCRIPTION OF THE DRAWINGS

The disclosed inventions will be described with reference to the accompanying drawings, which show important sample embodiments of the invention and which are incorporated in the specification hereof by reference, wherein.

DETAILED DESCRIPTION OF SAMPLE EMBODIMENTS

Figure 1:
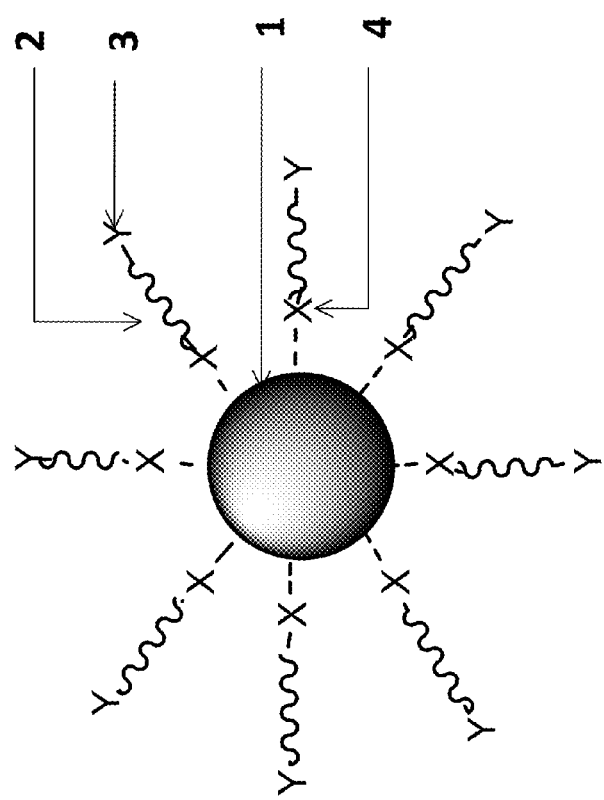
FIG. 1 schematically shows an example structure of a highly stable and chemically reactive metal nanostructure platform (SCRAP) in accordance with the disclosure.

The numerous innovative teachings of the present application will be described with particular reference to presently preferred embodiments (by way of example, and not of limitation). The present application describes several inventions, and none of the statements below should be taken as limiting the claims generally.

For simplicity and clarity of illustration, the drawing figures illustrate the general manner of construction and description, and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

It is contemplated and intended that the described structures and processes may be used for other suitable metal nanoparticles and their applications; for clarity reason, the examples are given based on gold nanoparticles. An ordinary person in the art would know the variations to modify the processes and reactions for other types of metal nanoparticles and their applications.

Nanoparticles as described are a cluster of metal elements having a metallic core, which may include, but not limited to, gold, silver, platinum, iron or copper. The diameters of the nanoparticle cores may range between 1~250 nm, and preferably, 5~100 nm. These metallic nanoparticles have unique optical, electrical and chemical properties and have been used extensively as the probes to detect bio-molecules such as proteins, DNAs, enzymes and/or hormones.

To detect a specific biomolecule, these nanoparticles are typically coated with target specific bio-probe molecules, such as a fragment of DNA or ligand recognizing molecules, for example, an antibody. Coated probe/ligand molecules locate and recognize targets, with the help of unique signal of the conjugated metal nanoparticles, targeted biomolecules are easily identified and measured.

Traditional methods to make gold nanoparticle based bioprobes are based on the non-specific absorption of the target-specific ligands, such as antibodies, nucleic acid, proteins or peptides to the surface of the metal core via non-specific chemical and physical static interactions. However, the optimal binding conditions depend on many factors including salt concentration, buffer solutions, pH and stabilizing agents. Also, during the process, freshly produced gold particles are not stably dispersed in a solution, they tend to aggregate and form large precipitates. In addition, nanoparticle bound bioprobes generated from these methods usually suffer poor stability and the probe molecules can easily detach from the metal core surface, thus losing their detection capability and producing high background or high non-specific signals.

In order to conjugate the bio-probe molecules strongly to the surface of the metal nanoparticles, a bi or multi functional polymeric coating material is first attached to the metal core surface via metal core binding motifs, which form anchors on the surface of the metal core to tether probe molecules covalently.

FIG. 1 shows such an example gold nanostructure. The coating molecule comprises a spacer region 2, a metal core binding motif (X) 4 and chemical reactive motif (Y) 3. In one example, the Motif X may have high affinity to the surface of the gold particle 1, while motif Y is either protected from reaction or does not have high affinity to the gold metal surface. For example the motif X may be such reactive groups such as thiols, amines and carboxylic groups while the motif Y is of $-NH_2$, $-COOH$, $-CHO$, $-NHNH_2$, epoxyl, vinyl, etc.

In another example, motif X and motif Y are similar or of the same chemical groups, but there are excessive amount of chemical reactive groups on the coating molecule. After sufficient number of active binding groups bind to the metal core surface, the excessive reactive groups remain to be free, and can be used for covalently linking bio-probe molecules to the metal core surface.

The coating molecules may be large polymers, for example, multi-functional polysaccharides, including modified dextrans, modified polyethylene glycols, and modified polyvinyl alcohols, etc.

Figure 2:
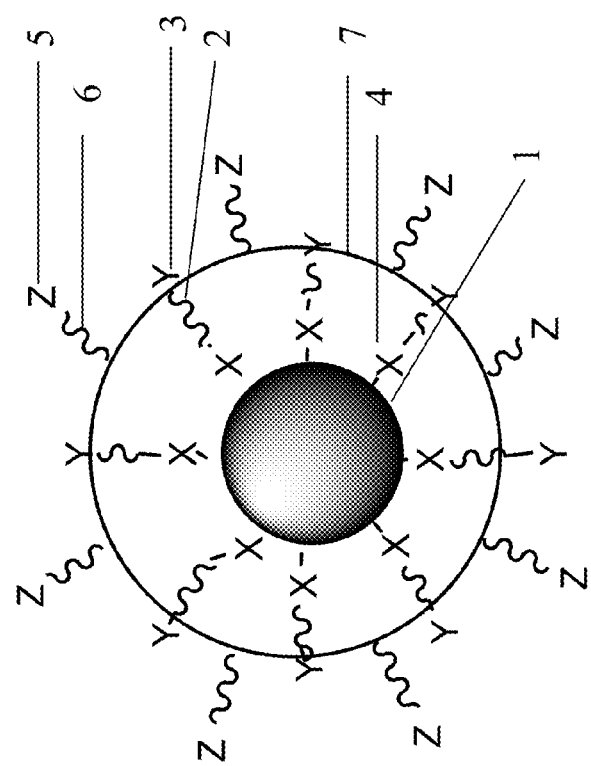
FIG. 2 schematically shows an example structure of a cross-linked, chemically reactive gold nanostructure in accordance with the disclosure.

To further stabilize the coating to the gold metal surface, the bound coating molecules on the metal core surface may be cross-linked together with a cross-linker agent forming an example nanoparticle structure shown in FIG. 2. When cross-linking molecule 7 is added to the solution of the formed nanostructure of FIG. 1, it reacts with some of other free functional groups, for example the group Y, forming a cross-linked matrix between the bound coating molecules on the surface of the metal core, greatly strengthening the coating molecules to the surface of the metal core.

After the coating, the static electrical charge of on the surface of the metal core particles are mostly neutralized, the tendency to aggregate and precipitate is reduced to minimal, and the resulted nanoparticle suspension solution is stable for storage and for further immediate use.

In one example, the remaining free Y functional groups are further used to covalently conjugate target-specific bio-molecules. In another example, further reactive groups (Z) 5 may be linked to the cross-linker 7, and reactive Z groups are then used to covalently conjugate the target-specific probe molecules.

The nanoparticle coating molecules may be obtained from natural or synthetic biocompatible polymers or derivatives of sulfhydryl and amino derived dextran, cyclo-dextran or other polysaccharides, sulfhydryl and amino derived polyethylene glycol, polyvinyl alcohol, polyacrylic acids. The binding motifs are a plural of nanoparticle surface reactive chemical groups. In one embodiment, reduced or non-reduced sulfhydryl groups are generated for gold nanoparticle surface binding. Binding of sulfhydryl groups to gold surface is well known. Other binding motifs include amines or carboxylic groups.

Cross-linker molecules may be a group of molecules which have at least two reactive groups that will react with other chemical groups. For example, glutaraldehyde, a chemical molecule with two aldehyde groups, can simultaneously react with the amine groups on two neighboring coating molecules and cross-link the neighboring amines. Cross-linked materials bind even tighter to the metal core of the nanoparticles and thus less likely fall off the metal core, preventing aggregation of the metal nanoparticles against different pH, salt concentration or even harsh chemical reactions.

Figure 3:
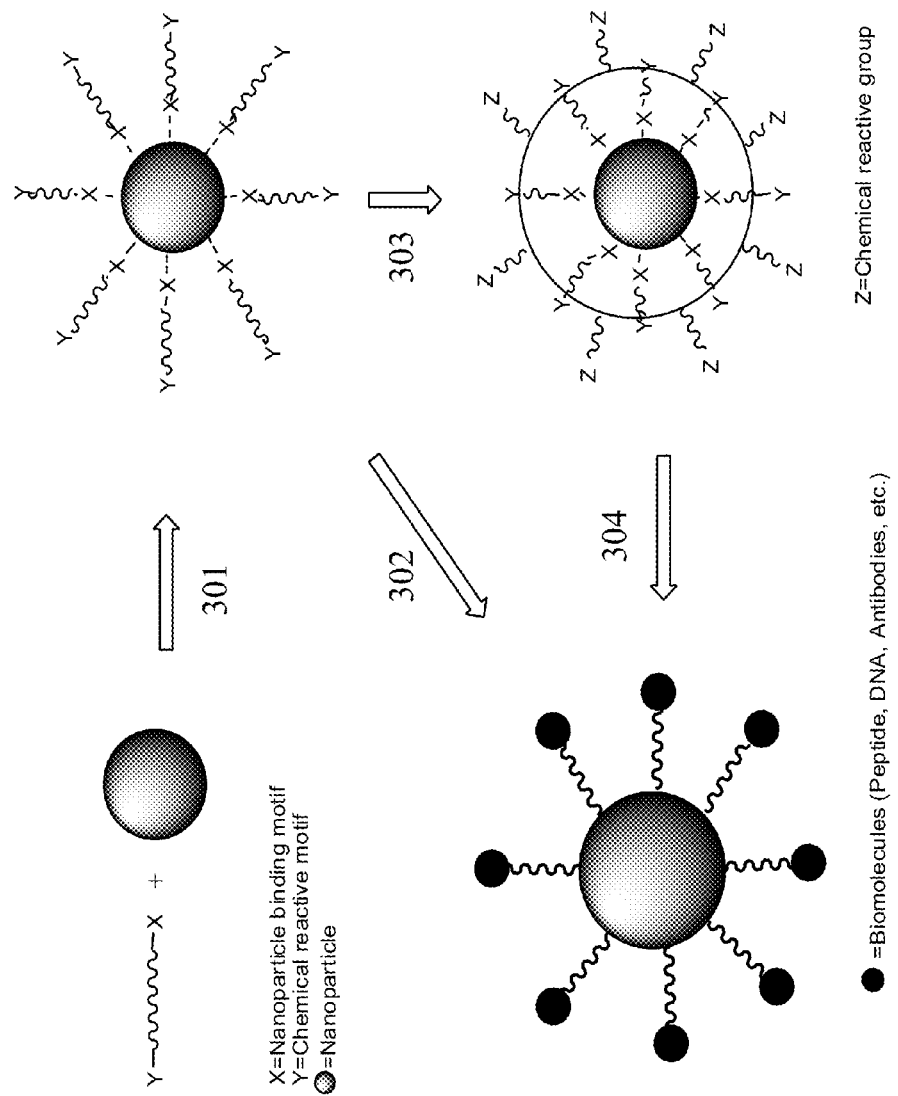
FIG. 3 schematically shows example steps of covalently conjugating bio-probe molecules to the stabilized metal nanostructure in accordance with the disclosure.

FIG. 3 shows example steps of producing a stabilized and chemically reactive gold nanostructure and its derived covalently ligand bound gold nanoparticle. After obtaining the coating polymer molecule that has both metal core binding motif and chemical reactive motif, the coating molecules are mixed with freshly generated metal nanoparticles at step 301. Due to the high affinity interactions between the metal binding motif, such as a thiol group, and the metal surface, the coating molecules are stably bound to the metal core surface while the chemical reactive groups, such as a —$NH_2$, remain free. This step also neutralizes the static charge of free electrons of the metal core, resulting in a stabilized metal nanoparticle solution.

The obtained coated metal nanoparticles may be further treated with a cross-linker agent at step 303, resulting a cross-linked matrix coating on the surface of the metal core, greatly enhancing the strength of the coating on the metal surface of the metal core.

Such stabilized and chemically reactive metal nanoparticle system is then used for conjugating target specific probe molecules at step 302, where the probe molecules can covalently be bonded to the surface of the metal nanoparticle.

EXAMPLES

Example 1

Stabilized Chemical Reactive Gold Nanoparticle Cluster

A. Preparation of 12 nm Gold Nanoparticles

Materials: Hydrogen tetrachloroaurate (III) hydrate and sodium citrate dehydrate were purchased from SIGMA ALDRICH® and used as received. All water used is deionized water. All glassware were cleaned in aqua regia and rinsed with distilled water before use.

4 ml of a 1% $HAuCl4$ solution in double distilled water is mixed with 4 ml of 0.1 $K2CO3$ and 100 ml deionized water, the mixture was cooled on ice. With rapid stirring of above solution on ice, 1 ml of a 7% sodium ascorbate aqueous solution was quickly added to the mixture and the total reaction volume was then brought to 400 ml with deionized water. The mixture was then heated to boil and refluxed until the color of the suspension turns from purple-red to red. The solution was then cooled to room temperature and filtered through a 0.22 um membrane. The red solid gold particles were then re-suspended in 12 ml water.

B. Synthesizing Thiolated Amino Dextrans

Dextrans with amino groups were purchased from NANOCS®. N-succinimidyl S-acetylthioacetate (SATA) was obtained from THERMOFISHER®. All chemicals were used as received.

Amino dextran (MW 40 kD) was dissolved at a concentration of 5 mg/ml in 50 mM sodium phosphate buffer containing 10 mM EDTA. SATA reagent was dissolved in DMSO at a concentration of 65 mM. 10 µl SATA solution was added to each ml of dextran solution and mixed and reacted for 30 min at room temperature. The reaction solution was dialyzed against large volume of deionized water. The acetylated —SH groups were then deprotected by adding 100 µl of 0.5 M hydroxylamine hydrochloride. The reaction was kept at room temperature for 2 hrs. The resulted reaction was then dialyzed against deionized water. The thiolated amino dextran was then freezing dried for future use.

C. Synthesizing Dextran Coated Gold Nanoparticles with Reactive Amine Groups.

Figure 4:
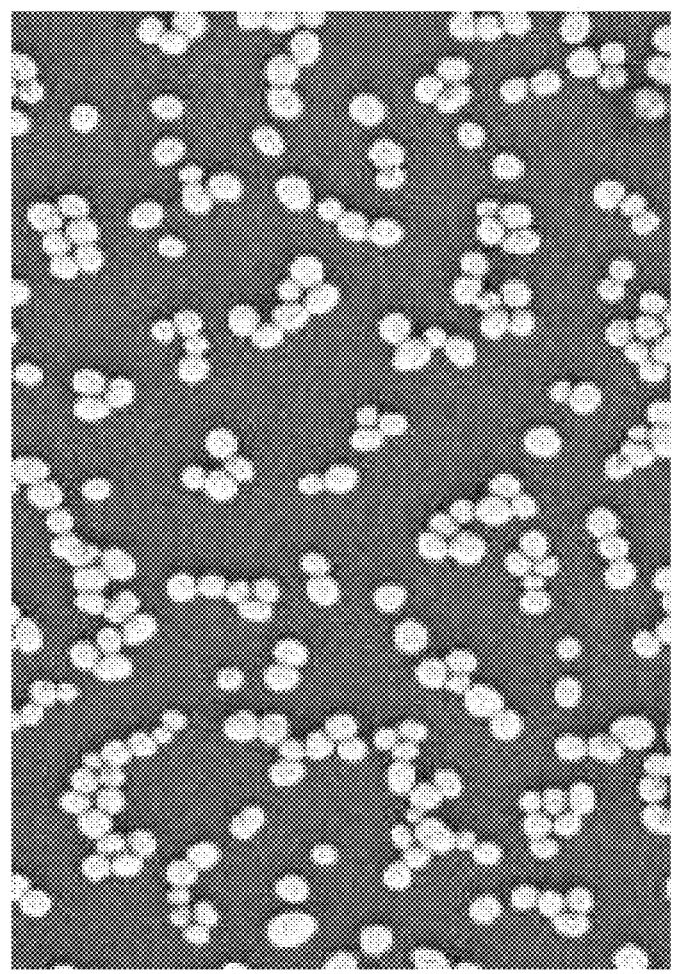
FIG. 4 shows a SEM photo picture of a solution of amino and thiol dextran functionalized gold nanoparticles, 20 nm in diameter.

Thiolated amino dextran was dissolved in water at the concentration of 1 mg/ml. 0.5 ml the above dextran solution was mixed gently with 10 ml 12 nm gold nanoparticle solution as prepared in section A. The mixture was placed at room temperature for 30 min. Then the dextran coated gold nanoparticles were separated from the reaction by centrifuging in semi-permeable membrane filter for 3 times. An example result of the amino dextran coated gold nanoparticles is shown in FIG. 4.

D. Cross-Linked and Amine Functionalized Gold Nanoparticles

50 µl 10% glutaraldehyde PBS solution was mixed with 1 ml of the above dextran coated gold nanoparticle solution, and reacted at room temperature for 1 hr. The non-reacted glutaraldehyde was removed by size exclusion chromatography eluted with PBS buffer. Then 10 µl diamino tetraethylene glycol was added to 1 ml of the purified cross-linked gold nanoparticle solution and reacted for 1 hr at room temperature. The reaction was then reduced with sodium boronhydride. Final product was purified through size exclusion column eluted with PBS buffer.

Example 2

A. Synthesizing PEG Coated Gold Nanoparticles with Reactive Carboxylic Groups on their Surfaces Thiol carboxylic heterobifunctional polyethylene glycol was obtained from NANOCS® Inc. A solution of thiol carboxylic PEG was prepared at the concentration of 1 mg/ml in deionized water. 0.5 ml above solution was added into 10 ml 12 nm gold nanoparticle solution prepared in Example 1. The mixture was gently shaken for 30 min at room temperature. The PEG coated gold nanoparticles was by centrifuging in semi-permeable membrane filter for 3 times.

Example 3

Synthesizing Nanoprobes Using Chemically Reactive Gold Nanoparticles

A. Preparation of Biotin Labeled Gold Nanoparticles

100 µl biotin DMSO solution (100 mM) was added to 1 ml carboxylic gold nanoparticle solution prepared in Example 2. 100 ul EDC (100 mM) and NHS (100 mM) were added subsequently. The reaction was mixed well and reacted for 2 hours at room temperature. Biotinylated gold nanoparticles were eluted from sephadex G-25 column with PBS buffer, pH 7.4. For 30 nm gold nanoparticles, the labeling rate of biotin is about 42 biotins/particle as determined by ELISA method using HRP labeled streptavidin (picture not shown).

B. Preparation of Streptavidin Labeled Gold Nanoparticles

Figures 5A, 5B:
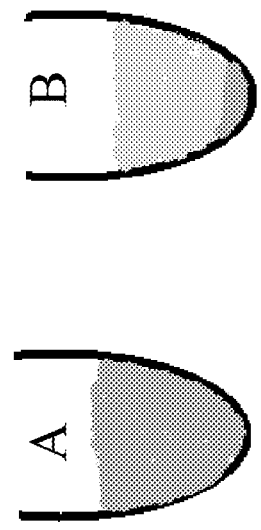
FIG. 5 schematically shows 10% salt test on an example streptavidin attached gold nanoparticles (30 nm) via covalent chemistry using the modified gold nanoparticles generated in accordance with FIG. 1.

100 µl streptavidin (1 mg/ml in PBS, pH 7.4) was added to 1 ml carboxylic gold nanoparticle solution. 100 µl EDC (100 mM) and NHS (100 mM) were added subsequently. The reaction was mixed well and reacted for 2 hrs at room temperature. Streptavidin conjugated gold nanoparticles were eluted from sephadex G-25 column with PBS buffer, pH 7.4. For 30 nm gold nanoparticles, the labeling rate of streptavidin is about 8 streptavidin/particle as determined by ELISA method using Biotin labeled HRP. FIGS. 5A and 5B show a schematic description of salt test on streptavidin labeling of coated gold nanoparticles. Streptavidin reacted with fully coated gold nanoparticles and the resulted labeled gold nanoparticle remained stable suspensions in 10% NaCl solution (FIG. 5A) while the incubation of streptavidin with non-coated nanoparticles formed aggregate precipitations in 10% NaCl (FIG. 5B).

According to various embodiments, there is provided: a method for generating probe specific polymer coated metal nanoparticle, comprising the actions of: obtaining a coating polymer molecule that has at least one metal core binding motif and at least one chemically reactive functional motif, wherein the chemically reactive functional motif is capable of forming covalent bonds with a specific probe molecule; obtaining a sufficiently sized metal nanoparticle having metal surface; reacting said coating polymer molecule with said metal nanoparticle under conditions that the metal core binding motif binds to the metal surface of the metal nanoparticle; and purifying the chemically reactive metal nanoparticle that is bound with the coating polymer molecule.

There is provided: the method above wherein said metal nanoparticle is made of metal selected the group consisting of gold, silver, copper, iron, and platinum; wherein said metal nanoparticle has a diameter between 1-250 nm, and said metal nanoparticle preferably has a diameter between 5-100 nm; wherein said coating polymer is selected from the group consisting of the derivatives of dextrans, cyclo-dextrans, polyethylene glycols, polyvinyl alcohols, dendrimer, and polyacrylic acid; wherein said chemically reactive functional motif is selected from the group consisting of amines, thiols, carboxylic groups, aldehydes, epoxys, maleimides, azides, hydrazides, tosylates, acrylates and carbohydrates; wherein said binding motif is a reduced or non-reduced sulfhydryl group; wherein said binding motif is a primary or secondary amine group; wherein said binding motif is a carboxylic group.

The above provided method further comprises the action of cross-linking said coating polymer after reacting with the metal nanoparticle with a cross-linker reagent; and the actions of: reacting said chemically reactive polymer coated metal nanoparticle with a specific probe molecule under conditions favorable for the chemically reactive functional group to have chemical reaction and form covalent bonds with the probe molecule; and purifying the probe-bound metal nanoparticle.

According to various embodiments, there is provided: a metallic nanostructure, comprising: a metallic core having a metal surface; at least one coating polymer molecule that binds to the metal surface via at least one metal core binding motif; and at least one free chemically reactive functional moiety that is covalently attached to said coating polymer; wherein said metal core is made of metal selected the group consisting of gold, silver, copper, iron, and platinum; wherein said metal core has a diameter between 1-250 nm; said metal nanoparticle has a preferred diameter between 5-100 nm; wherein said coating polymer is selected from the group consisting of the derivatives of dextrans, cyclo-dextrans, polyethylene glycols, polyvinyl alcohols, dendrimer acrylic acid and polyacrylic acid; wherein said chemically reactive functional moiety is a chemical reactive moiety selected from the group consisting of amines, thiols, carboxylic groups, aldehydes, epoxys, maleimides, azides, hydrazides, tosylates, acrylates and carbohydrates; wherein said binding motif is a reduced or non-reduced sulfhydryl group; wherein said binding motif is primary or secondary amine; wherein said binding motif is a carboxylic group; wherein at least two said coating polymer molecules bind to the metal surface via each of their binding motifs, and are cross-linked with each other via said a cross-linker reagent.

The provided metallic nanostructure further comprises: a specific probe molecule covalently bonded with the coating polymer molecule by forming covalent bonds with the chemically reactive functional moiety. As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims. Additional general background, which helps to show variations and implementations, may be found in the following publications, US 2009/02981115 A1, U.S. Pat. No. 6,677,122, and U.S. Pat. No. 7,588,827, all of which are hereby incorporated by reference herein for all purposes.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for generating polymer coated and chemically active metal nanoparticle, comprising the actions of:
   obtaining a plurality of coating polymer molecules that each of said coating polymer molecules has at least one metal core binding motif and at least one chemically reactive functional motif, wherein the chemically reactive functional motif is capable of forming covalent bonds with a specific probe molecule;
   obtaining a sufficiently sized metal nanoparticle having a metal surface;
   reacting said plurality of coating polymer molecules with said metal nanoparticle under conditions that the metal core binding motif binds to the metal surface of the metal nanoparticle to generate a chemically reactive metal nanoparticle bound with the plurality of PEG coating polymer molecules;
   purifying the chemically reactive metal nanoparticle bound with the plurality of coating polymer molecules; and
   reacting said chemically reactive metal nanoparticle with a cross-linker agent so that said plurality of coating polymer molecules covalently cross-linked with each other through said cross-linker agent, forming a chemically reactive polymer coated nanoparticle with a coating layer covering said metal surface of said metal nanoparticle.

2. The method of claim 1, wherein said metal nanoparticle is made of metal selected from the group consisting of gold, silver, copper, iron, and platinum.

3. The method of claim 1, wherein said metal nanoparticle has a diameter between 1-250 nm.

4. The method of claim 1, wherein said metal nanoparticle has a diameter between 5-100 nm.

5. The method of claim 1, wherein said coating polymer is selected from the group consisting of the derivatives of dextrans, cyclo-dextrans, polyethylene glycols, polyvinyl alcohols, dendrimer, and polyacrylic acid.

6. The method of claim 1, wherein said chemically reactive functional motif is selected from the group consisting of amines, thiols, carboxylic groups, aldehydes, epoxys, maleimides, azides, hydrazides, tosylates, acrylates and carbohydrates.

7. The method of claim 1, wherein said metal core binding motif is a reduced or non-reduced sulfhydryl group.

8. The method of claim 1, wherein said metal core binding motif is a primary or secondary amine group.

9. The method of claim 1, wherein said metal core binding motif is a carboxylic group.

10. The method of claim 1, wherein said cross-linker reagent is glutaraldehyde.

11. The method of claim 1, further comprising the actions of:
reacting said chemically reactive polymer coated metal nanoparticle with a specific probe molecule under conditions favorable for the chemically reactive functional group to have chemical reaction and form covalent bonds with the probe molecule to generate a probe-bound metal nanoparticle; and
purifying the probe-bound metal nanoparticle.

12. A metallic nanostructure, comprising:
a metallic core having a metal surface;
a plurality of coating polymer molecules that bind to the metal surface via at least one metal core binding motif;
at least one other chemically reactive functional moiety covalently attached to each of said coating polymer molecules; and
a plurality of cross-linker molecules;
wherein said plurality of coating polymer molecules are covalently cross-linked with each other through said plurality of cross-linker molecules, forming a coating layer covering said metal surface.

13. The metallic nanostructure of claim 12, wherein said metal core is made of metal selected from the group consisting of gold, silver, copper, iron, and platinum.

14. The metallic nanostructure of claim 12, wherein said metal core has a diameter between 1-250 nm.

15. The metallic nanostructure of claim 12, wherein said metal core has a diameter between 5-100 nm.

16. The metallic nanostructure of claim 12, wherein said coating polymer is selected from the group consisting of the derivatives of dextrans, cyclo-dextrans, polyethylene glycols, polyvinyl alcohols, dendrimer acrylic acid and polyacrylic acid.

17. The metallic nanostructure of claim 12, wherein said chemically reactive functional moiety is a chemical reactive moiety selected from the group consisting of amines, thiols, carboxylic groups, aldehydes, epoxys, maleimides, azides, hydrazides, tosylates, acrylates and carbohydrates.

18. The metallic nanostructure of claim 12, wherein said binding motif is a reduced or non-reduced sulfhydryl group.

19. The metallic nanostructure of claim 12, wherein said binding motif is primary or secondary amine.

20. The method of claim 12, wherein said binding motif is a carboxylic group.

21. The metallic nanostructure of claim 12, wherein said cross-linker is glutaraldehyde.

22. The metallic nanostructure of claim 12, further comprising:
a specific probe molecule covalently bonded with the coating polymer molecule by forming covalent bonds with the chemically reactive functional moiety.

* * * * *